United States Patent
Lohner et al.

(10) Patent No.: US 9,086,355 B2
(45) Date of Patent: Jul. 21, 2015

(54) ULTRASONIC SENSOR FOR VALUE DOCUMENTS, TRANSDUCER MODULE FOR SAID SENSOR, AND METHOD FOR MANUFACTURING THE ULTRASONIC SENSOR

(75) Inventors: Joseph Lohner, München (DE); Hans-Uwe Moosler, München (DE); Ernst Rausch, Dorfen (DE); Walter Berngeher, Olching (DE)

(73) Assignee: GIESECKE & DEVRIENT GMBH, Munich (DE)

( * ) Notice: Subject to any disclaimer, the term of this patent is extended or adjusted under 35 U.S.C. 154(b) by 361 days.

(21) Appl. No.: 13/808,197

(22) PCT Filed: Jul. 6, 2011

(86) PCT No.: PCT/EP2011/003352
§ 371 (c)(1),
(2), (4) Date: Jan. 3, 2013

(87) PCT Pub. No.: WO2012/003974
PCT Pub. Date: Jan. 12, 2012

(65) Prior Publication Data
US 2013/0104660 A1 May 2, 2013

(30) Foreign Application Priority Data
Jul. 7, 2010 (DE) .......................... 10 2010 026 341

(51) Int. Cl.
*G01D 18/00* (2006.01)
*G01N 29/04* (2006.01)
(Continued)

(52) U.S. Cl.
CPC .................. *G01N 29/04* (2013.01); *G07D 7/08* (2013.01); *G10K 11/004* (2013.01); *Y10T 29/49007* (2015.01)

(58) Field of Classification Search
CPC ...... G07D 7/08; G01N 29/04; Y10T 29/49007
USPC ............................................... 73/632; 29/595
See application file for complete search history.

(56) References Cited

U.S. PATENT DOCUMENTS 6,323,583 B1 * 11/2001 Gunther et al. ............... 310/330
7,696,671 B2 * 4/2010 Sawada et al. ................ 310/334
(Continued)

FOREIGN PATENT DOCUMENTS

DE 10 2006 043 882 A1 3/2008
DE 10 2008 038 336 A1 2/2009
(Continued)

OTHER PUBLICATIONS

German Search Report for DE 10 2010 026 341.9, Mar. 15, 2011.
(Continued)

*Primary Examiner* — J M Saint Surin
(74) *Attorney, Agent, or Firm* — Workman Nydegger (57) ABSTRACT

An ultrasonic transducer module for an ultrasonic sensor for detection and/or examination of value documents which includes at least one piezoelectric ultrasonic transducer with electrical connecting strands, and a mounting module for holding the ultrasonic transducer for mounting on a connection support. The mounting module has conducting paths which are electrically connected to the connecting strands of the ultrasonic transducer and which have contact areas which are so configured that the ultrasonic transducer module is placeable for mounting onto a surface of the connection support on which there are located contact areas complementary to the conducting path contact areas, with the contact areas and the complementary contact areas being solderable to each other.

11 Claims, 5 Drawing Sheets

(51) Int. Cl.
*G07D 7/08* (2006.01)
*G10K 11/00* (2006.01)

(56) References Cited

U.S. PATENT DOCUMENTS

| | | | |
|---|---|---|---|
| 2006/0241474 A1* | 10/2006 | Kawashima et al. | 600/459 |
| 2007/0237031 A1* | 10/2007 | Kawashima et al. | 367/140 |
| 2008/0088206 A1 | 4/2008 | Watanabe | |
| 2009/0054784 A1 | 2/2009 | Okuda et al. | |
| 2010/0005888 A1 | 1/2010 | Domke et al. | |

FOREIGN PATENT DOCUMENTS

| | | | |
|---|---|---|---|
| GB | 2128399 | * | 4/1984 |
| JP | 09222454 A | * | 9/1997 |

OTHER PUBLICATIONS

International Search Report for PCT/EP2011/003352, Nov. 12, 2012.
International Preliminary Report on Patentability and Written Opinion for PCT/EP2011/003352, Feb. 5, 2013.

* cited by examiner

ULTRASONIC SENSOR FOR VALUE DOCUMENTS, TRANSDUCER MODULE FOR SAID SENSOR, AND METHOD FOR MANUFACTURING THE ULTRASONIC SENSOR

BACKGROUND OF THE INVENTION

A. Field of the Invention

The present invention relates to an ultrasonic transducer module for an ultrasonic sensor for detection and/or examination of value documents, to an ultrasonic sensor for detection and/or examination of value documents having such an ultrasonic transducer module, and to a method for manufacturing the ultrasonic sensor.

B. Related Art

Value documents are understood in this connection to be sheet- or card-shaped objects that represent for example a monetary value or an authorization and hence should not be manufacturable arbitrarily by unauthorized persons. Hence, they have features that are not simple to produce, in particular to copy, whose presence is an indication of authenticity, i.e. manufacture by an authorized body. Important examples of such value documents are chip cards, coupons, vouchers, checks and in particular bank notes.

Upon the machine processing of such value documents, in particular of bank notes, ultrasound is frequently used. Ultrasound can be used for example for detecting value documents, i.e. for recognizing the passing of a value document upon transport, and/or for examining value documents, for example for recognizing so-called double removals, i.e. incompletely singled value documents of a value-document stack or bundle, or value documents transported in partial overlap, and/or for capturing ultrasonic properties of the value document, for example for ascertaining the state of the value documents. In so doing, ultrasound is first coupled into air by a transducer, is then propagated in the air until impinging on a value document, where applicable, and is then remitted or transmitted by the value document. The ultrasound thus emitted by the value document can then be captured again. Due to the necessary coupling into air and the decrease in coupling efficiency with increasing ultrasonic frequency, the ultrasound employed usually does not have a very high frequency. Ultrasound is hence understood within the scope of the present application to be sound with frequencies between 40 kHz and about 1 GHz.

For generating and receiving such ultrasound there are employed, at least in the area of detecting and/or examining value documents, piezoelectric ultrasonic transducers which convert electrical vibrations into mechanical or sound vibrations employing a piezoelectric element. So as not to impair their vibration upon the generation or reception of the ultrasound, they possess connecting strands, i.e. very flexible connecting wires, which are electroconductively connected to the piezoelectric element only indirectly or directly. Hence, ultrasonic transducers with rigid connecting pins are typically not employed. Common piezoelectric elements have a temperature resistance up to about 80° C. or 90° C., so that they must be treated very gently upon the manufacture of sensors.

The thus described ultrasonic sensors are not simple to manufacture, however, because the connecting strands must be contacted to conducting paths on a circuit board which usually has further circuit elements as well.

SUMMARY OF THE DISCLOSURE

Hence, the invention is based on the object of providing means and methods that make ultrasonic sensors for detection and/or examination of value documents simple to manufacture, and of providing a corresponding ultrasonic sensor.

This object is achieved by an ultrasonic transducer module for an ultrasonic sensor for detection and/or examination of value documents which comprises at least one piezoelectric ultrasonic transducer with electrical connecting strands, and a mounting module for holding the at least one ultrasonic transducer and for mounting on a connection support, wherein the mounting module has conducting paths which are electrically connected to the connecting strands of the at least one ultrasonic transducer and which have contact areas which are so configured that the ultrasonic transducer module is placeable for mounting onto a surface of the connection support on which surface there are located contact areas complementary to said contact areas, and the contact areas and the complementary contact areas are respectively solderable to each other.

The object is further achieved by an ultrasonic sensor for detection and/or examination of value documents having an ultrasonic transducer module according to the invention and a connection support with contact areas complementary to the contact areas of the ultrasonic transducer module, wherein the contact areas of the ultrasonic transducer module and the complementary contact areas of the connection support are soldered to each other. The ultrasonic sensor can be configured in particular for detecting value documents, in particular for detecting an edge of a value document transported past it or through it, and/or for detecting double removals, and/or for examining value documents, i.e. in particular for capturing ultrasonic properties thereof.

The ultrasonic transducer module according to the invention has the mounting module which holds the at least one piezoelectric ultrasonic transducer which in turn has electrical connections in the form of connecting strands or slightly flexible connecting wires, but not connecting pins. It is intended to be mounted on or against a suitably specified connection support which serves as a support for the mounting module as well as for its electrical connection. Thus it also serves to mount the ultrasonic transducer.

The ultrasonic transducer module is further characterized by having conducting paths which are electrically connected, preferably soldered, to the connecting strands of the at least one ultrasonic transducer. The conducting paths can be configured for example as conducting paths on a circuit board or also at least partly in the form of wires. The conducting paths have contact areas which serve to form soldered connections for electrical connection. The connection support likewise has for this purpose conducting paths which have contact areas complementary to the contact areas of the ultrasonic transducer module and are arranged on a surface or a surface region of the connection support onto which the mounting module is placed for mounting. The contact areas and the complementary contact areas are so mutually coordinated that the ultrasonic transducer module is placeable for mounting onto the surface of the connection support, and the contact areas and the complementary contact areas are solderable to each other. The position of the contact areas and that of the complementary contact areas can be mutually coordinated by configuration and position of the contact areas on the mounting module or configuration and position of the complementary contact areas of the connection support being specified and the respective other part being configured accordingly.

The connection support can in particular have, besides contact areas provided for the electrical connection of the mounting module, further electrical or electronic components, including a processor or an FPGA, where applicable.

For the connection support to be able to serve as a support for the mounting module, the forms of the connection support and of the mounting module are so mutually coordinated that the mounting module is mechanically fastenable on the connection support. In particular, at least one region of a surface of the connection support can be configured accordingly.

For mounting the ultrasonic transducer module, the latter only needs to be placed onto the surface or the surface region of the connection support, so that a soldering of the contact areas to the complementary contact areas is possible. Because the mounting module and the connection support are rigid compared to the connecting strands, at least in the region of the contact areas or complementary contact areas, the soldered connection is simple to produce, even when the connection support is large or already has other components. This allows the production of the ultrasonic module to be completed and to be checked, in particular the critical contacting between the connecting strands and the contact areas to be checked, before the ultrasonic transducer module is fastened on the connection support. This necessitates only the handling of the mounting module and of the at least one ultrasonic transducer.

Hence, the object is also achieved by a method for manufacturing an ultrasonic sensor for detection and/or examination of value documents having the steps of: manufacturing an ultrasonic transducer module according to the invention, checking the contacting between the connecting strands and the contact areas of the mounting module, placing the ultrasonic transducer onto a connection support with contact areas complementary to the contact areas of the ultrasonic transducer module, and soldering the contact areas and the complementary contact areas.

In principle, the ultrasonic transducer module according to the invention only needs to have one ultrasonic transducer. However, the ultrasonic transducer module preferably has, in addition to the at least one ultrasonic transducer, at least one further piezoelectric ultrasonic transducer with electrical connecting strands, the mounting module is configured for holding the ultrasonic transducers, and has conducting paths which are electrically connected to the connecting strands of the further ultrasonic transducer and have further contact areas which are so configured that the ultrasonic transducer module is placeable for mounting onto the surface of the connection support on which surface there are located further complementary contact areas for the further contact areas, and the further contact areas and the further complementary contact areas are solderable to each other. Such an ultrasonic transducer module permits the construction of an ultrasonic sensor in simple fashion even with several ultrasonic transducers.

The mounting module is configured, on the one hand, for holding the ultrasonic transducer or transducers and, on the other hand, for contacting with the connecting strands, and can otherwise be configured arbitrarily. Thus, the mounting module can have a transducer holder in which the ultrasonic transducer is held or the ultrasonic transducers are held, and a circuit board mechanically connected to the transducer holder and having the conducting paths. This embodiment allows the transducer holder to be manufactured especially simply, because it substantially only needs to perform mechanical functions. The employment of the circuit board permits a simple formation of the conducting paths by standard methods. The connection between the transducer holder and the circuit board can be produced arbitrarily, for example by form closure and/or force closure or by material closure, i.e. bonding.

Although the circuit board can in principle be configured arbitrarily, it can preferably have at least one through bore through which the connecting strands of the ultrasonic transducer are guided, or through bores through which the connecting strands of the ultrasonic transducers are guided. This permits a simple production of soldered connections between the connecting strands and the conducting paths.

Alternatively, the mounting module can have a one-pieced holding element in which and/or on the surface of which the conducting paths extend. The holding element thus performs the functions of the circuit board as well as of the transducer holder. This embodiment allows the manufacture of the ultrasonic transducer module to be simplified, in particular in the case of large quantities, because the working step of connecting the circuit board to the transducer holder is dispensed with. In particular, the holding element can be manufactured by injection molding.

The mounting module serves in particular for holding the ultrasonic transducer or transducers and can for this purpose have corresponding devices, for example one or several recesses or through holes in which the ultrasonic transducer or transducers are held. Hence, it also serves to align the ultrasonic transducers not only relative to the mounting module, but also relative to the connection support after mounting of the ultrasonic transducer module. Because in particular the alignment of the ultrasonic transducers relative to the mounting module can be checked before the mounting on the connection support, there can be obtained a simple alignment also relative to the connection support.

If the ultrasonic transducer module comprises at least two ultrasonic transducers held in the mounting module, the ultrasonic transducers can respectively have a transmission or reception characteristic for ultrasound. The ultrasonic transducers can thus, according to a first variant, be held in the mounting module, through corresponding configuration thereof, such that the transmission and reception characteristics are inclined at a specified angle relative to each other. In a second variant, the transmission and reception characteristics of the ultrasonic transducers can be aligned parallel to each other. For this purpose, the mounting module can be configured accordingly. This embodiment facilitates in particular the manufacture of ultrasonic sensors having at least two, preferably several, ultrasonic transducers which are to be aligned in specified fashion to each other with their transmission and reception characteristics.

For holding the ultrasonic transducer or transducers it is preferred that the ultrasonic transducer or transducers are held so as to be decoupled at least partly for vibrations, in particular in the ultrasonic frequency range, from the transducer holder. "Decoupled" is understood here to mean that vibrations are not transmitted, or not transmitted in full strength, from the ultrasonic transducer to the mounting module. For this purpose, the ultrasonic transducer or transducers can be held in the mounting module such that a damping occurs upon a transmission of vibrations between ultrasonic transducer and mounting module, and/or an impedance jump.

In principle, it can be sufficient that the mounting module is placed only onto the connection support and soldered thereon with the complementary contact areas. To increase the accuracy of the alignment of the ultrasonic transducer module on the connection support and for increased stability after mounting, however, it is preferred that the mounting module has at least one positioning element by means of which and of a complementary positioning element on or in the connection support the mounting module is positionable on the connection support. As a positioning element on the mounting module there can be provided for example a projection, in particular a pin; the connection support can then have as a complementary positioning element a corresponding depression, for example a recess or a hole, or in the case of a pin as a positioning element a bore. It is also possible that the configuration of the positioning element and that of the complementary positioning element are interchanged. The positioning element and the complementary positioning element must be arranged suitably relative to the contact areas and the complementary contact areas.

Also, the mounting module can preferably have a snapping or locking element, or the positioning element be configured as a snapping or locking element, by means of which the mounting module is fastenable on the connection support. This embodiment simultaneously offers the advantages that by producing the snapping or locking connection a simple mechanical mounting of the mounting module on the connection support is possible before a soldering of the contact areas, and furthermore a stable mechanical connection is produced which relieves the soldered connection.

DESCRIPTION OF THE DRAWINGS

The invention will hereinafter be explained further by way of example with reference to the drawings. There are shown:

FIG. 1 a schematic view of a value-document processing apparatus, in the example a bank-note sorting apparatus, FIG. 2 a schematic view of a portion of the bank-note processing apparatus in FIG. 1 having a transport apparatus for bank notes and an ultrasonic sensor with two ultrasonic transducer modules, FIG. 3 a perspective view of one of the ultrasonic transducer modules in FIG. 2, FIG. 4 a partly sectional view of the ultrasonic transducer module in FIG. 3 mounted on a connection support shown only partly, FIG. 5 a view of the side of the ultrasonic transducer module in FIG. 3 facing the connection support in FIG. 4, FIG. 6 a perspective view of a second ultrasonic transducer module which is a variant of the ultrasonic transducer module in FIG. 4, FIG. 7 a side view of the ultrasonic transducer module in FIG. 6 mounted on the connection support, FIG. 8 a partly sectional schematic view of a third ultrasonic transducer module, FIG. 9 a view of the side of the ultrasonic transducer module in FIG. 8 facing a connection support, FIG. 10 a partly sectional schematic view of a fourth ultrasonic transducer module, FIG. 11 a partly sectional schematic view of a fifth ultrasonic transducer module, and FIG. 12 a view of the side of the ultrasonic transducer module in FIG. 11 facing a connection support.

DETAILED DESCRIPTION OF EXEMPLARY EMBODIMENTS

Figure 1:
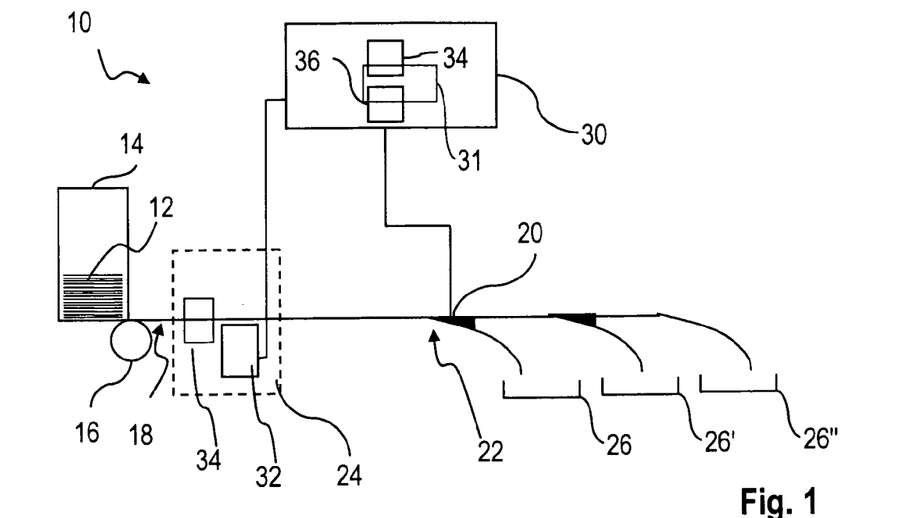

FIG. 1 shows an apparatus 10 for processing value documents, in the example a bank-note processing apparatus, which serves, inter alia, to ascertain the state and authenticity of value documents 12 in the form of bank notes. The apparatus 10 has an input pocket 14 for the input of value documents 12 to be processed, a singler 16 which can access value documents 12 in the input pocket 14, a transport device 18 having gates 20 and 20' arranged in succession along a transport path 22, and a respective output pocket 26, 26', 26" after each of the gates and at an end of the transport path 22 following the two gates. Along the transport path 22 given by the transport device 18 there is arranged before the gate 20 and after the singler 16 a sensor assembly 24 which serves to capture properties of value documents 12 supplied in singled form, and to form sensor signals representing the properties. A control device 30 is connected at least to the sensor assembly 24 and the gates 20 and 20' via signal connections and serves to evaluate sensor signals of the sensor assembly 24 and to control at least the gates 20 and 20' in dependence on the result of the evaluation of the sensor signals.

The sensor assembly 24 for this purpose comprises, in this embodiment example, an optical sensor 32 for locally resolved capture of color properties, which captures optical radiation remitted by the value document. The arrangement further comprises an ultrasonic sensor 34 for detection of value documents transported past it in transport direction T. In this example, it is configured more precisely for recognizing double removals, i.e. value documents that have been faultily or incompletely singled and hence overlap.

Figure 2:
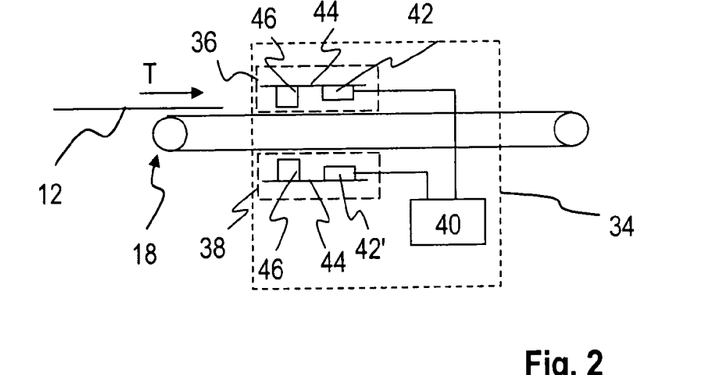

The ultrasonic sensor 34 is shown more precisely, but schematically, in FIG. 2. It is configured as a transmission sensor and thus comprises a transmitter portion 36 and a receiver portion 38 which are arranged on mutually opposing sides of the transport path 22, as well as a control and evaluation device 40, connected to the portions via signal connections, for controlling the transmitter portion 36 and for processing signals of the receiver portion 38. The portions 36 and 38 are like configured, except for electronic circuits 42 and 42', so that it is sufficient to describe only one of the portions more precisely.

The portion 36 has a connection support 44 in the form of a circuit board on which an ultrasonic transducer module 46 is attached and held. On the connection support 44 there are located conducting paths 48 which electrically connect the electrical circuit 42, a driver circuit for controlling the ultrasonic transducer module 46, and electrical connections of the ultrasonic transducer module 46. In the receiver portion 38, the electrical circuit 42' is a signal processing circuit which can comprise a processor or an FPGA and processes signals from the ultrasonic transducer module of the receiver portion and transfers them to the control and evaluation device 40.

Figure 3:
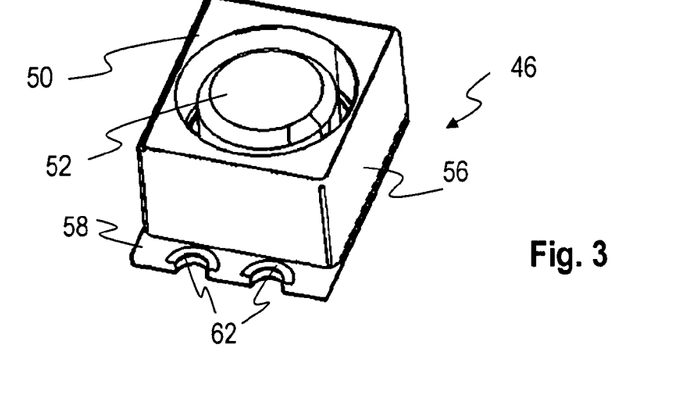
Figure 4:
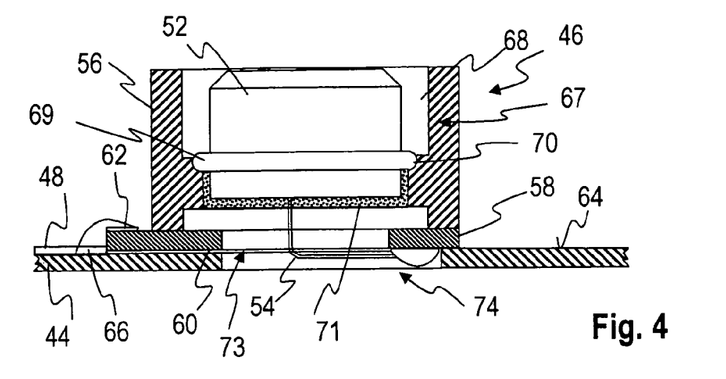
Figure 5:
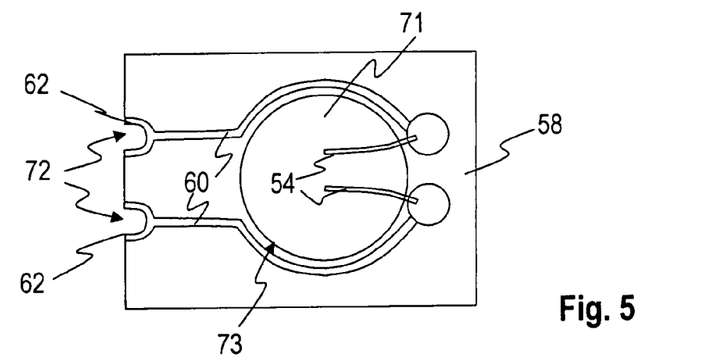

The ultrasonic transducer module 46 is shown more precisely in FIGS. 3 to 5. It has a mounting module 50 and, in this embodiment example, an ultrasonic transducer 52 which is held in the mounting module.

The ultrasonic transducer 52 is a piezoelectric ultrasonic transducer which has connecting strands 54 via which there are supplied electrical signals which the ultrasonic transducer converts to ultrasound at a specified frequency or in a specified frequency range, respectively between 40 kHz and 1 MHz, preferably between 100 kHz and 500 kHz. Upon employment in the receiver portion, the connecting strands 54 carry the voltages or currents arising through conversion of the received ultrasound to electrical voltages.

The mounting module 50, in the present embodiment example, comprises a transducer holder 56 in which the ultrasonic transducer 52 is held, and a circuit board 58 connected to the transducer holder 56 and having conducting paths 60. In FIG. 4 the transducer holder 56 and the circuit board 58 are shown sectionally, while the ultrasonic transducer 52 is shown in a side view. The mounting module 50 is altogether so configured that its conducting paths 60 are electrically connected to the connecting strands 54 of the at least one ultrasonic transducer 52, and that the conducting paths 60 have contact areas 62 which are so configured that the ultrasonic transducer module 46 is placeable for mounting onto a surface 64 of the connection support 44 on which surface there are located contact areas 66 complementary to the contact areas 62, and the contact areas 62 and the complementary contact areas 66 are solderable to each other.

The transducer holder 56 in addition has as a receiving means 67 for the ultrasonic transducer a through hole 68 with a circular cross section, which has a circumferential shoulder or groove 70 in its wall. In the through hole 68 the ultrasonic transducer 52, which has a groove corresponding to the shoulder or groove, is held by means of an elastic O-ring 69 so as to be decoupled at least partly from the transducer holder for ultrasonic vibrations. On the side of the ultrasonic transducer 52 where connecting strands 54 emerge therefrom, the through hole 68 is filled with an injected elastic compound 71, so that the ultrasonic transducer 52 is held in the transducer holder 56 reliably and aligned relatively thereto.

The transducer holder 56 can be manufactured as a molded part by injection molding or by machining of a suitable block of material.

The circuit board 58 possesses the conducting paths 60 which, in this embodiment example, are of approximately mirror-symmetric configuration. At one end they are electrically connected to the connecting strands 54 through a soldered connection; at the other end they end in the above-mentioned contact areas 62. In this embodiment example, the circuit board 58 has a bulge 72 for each of the conducting paths 60. The contact areas 60 extend from the underside of the circuit board 58, which is not in contact with the transducer holder 56, over the edge of the circuit board 58 up to the upper side of the circuit board 58 which has regions extending beyond the transducer holder 56. The conducting paths are shown in the figures only schematically, but not to scale. The circuit board 58 further has an opening 73 through which the connecting strands 54 can be guided into the region of the conducting paths 60.

The transducer holder 56 and the circuit board 58 are, in this embodiment example, connected to each other to form the mounting module 50 through an adhesive connection not shown.

The connection support 44 has, in this embodiment example, besides the contact areas 66 complementary to the contact areas 60, an optional aperture 74 which is so arranged relative to the complementary contact areas 66 and the ends of the conducting paths 60, when the mounting module is mounted, that the ends of the connecting strands 54 and their soldered connections to the conducting paths 60 are arranged within the aperture 74 and do not protrude on the underside (cf. FIG. 4).

For manufacturing the ultrasonic transducer module, the ultrasonic transducer 52 is first fastened in the transducer holder 56. Thereafter the transducer holder 56 is connected mechanically to the ultrasonic transducer 52. Then the connecting strands 54 are soldered to the conducting paths 60.

The mounting module can now be simply checked, for example as to whether there is a sufficient electrical connection between the contact areas 62 and the connecting strands 54 or the ultrasonic transducer 52.

After the check, the mounting module 50 can be placed for mounting onto the connection support 44 with the side facing away from the ultrasonic transducer 52, i.e. in FIG. 3 the underside of the circuit board 58 and, in this embodiment example, the side bearing the conducting paths 60, so that the contact areas 62 and the complementary contact areas 66 are neighboring. There can then be produced a soldered connection between these areas which, in this embodiment example, also serves to mechanically fasten the mounting module 40 on the connection support 44. Thus, the ultrasonic transducer 52 is aligned relative to the connection support 44, so that an elaborate readjustment can be dispensed with.

In principle, the transmission or reception direction of the ultrasonic transducer 52 can, in other embodiment examples, also form a different angle with the connection support 44, which can be obtained by changing the mounting of the mounting module or by changing the through hole.

Figure 6:
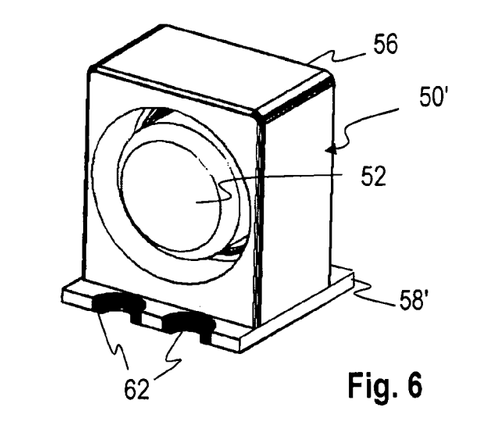
Figure 7:
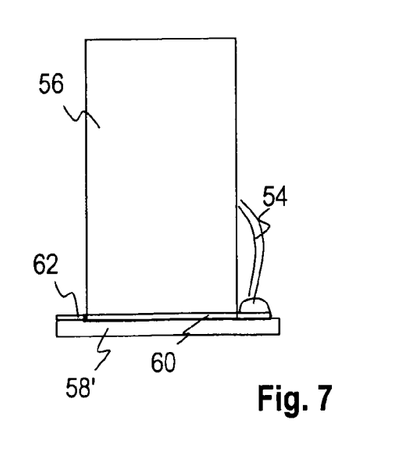

A variant of the preceding embodiment example is shown in FIGS. 6 and 7. Here, the mounting module 50' differs from the mounting module 50 only in that it can be mounted onto the connection support with one side such that the transmission or reception direction of the ultrasonic transducer 52 extends in a direction parallel to the connection support 44. In these figures, identical reference signs designate identical components as in the first embodiment example. In addition, in contrast with the first embodiment example, the circuit board 58' is configured shorter and the conducting paths extend on the side of the circuit board facing the ultrasonic transducer. However, the unchanged transducer holder 56 with the ultrasonic transducer 52 is now connected to the circuit board 58' with a narrow side through an adhesive connection. For mechanical mounting of the ultrasonic transducer module, an adhesive connection can be used here in addition to the soldered connection. Due to the different alignment of the ultrasonic transducer module relative to the connection support, the latter does not need to have an aperture.

Figure 8:
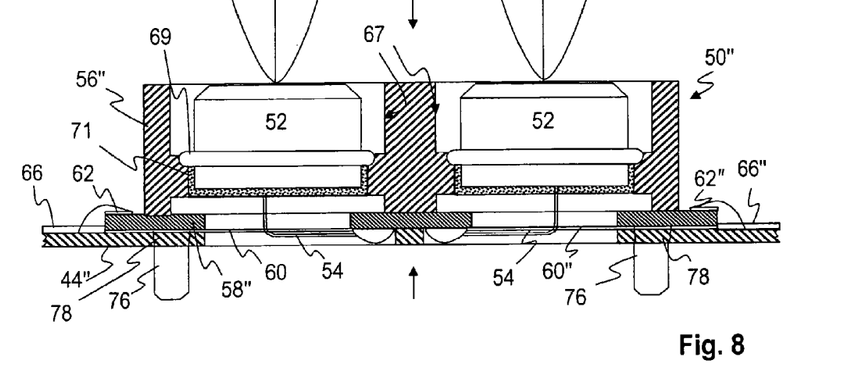
Figure 9:
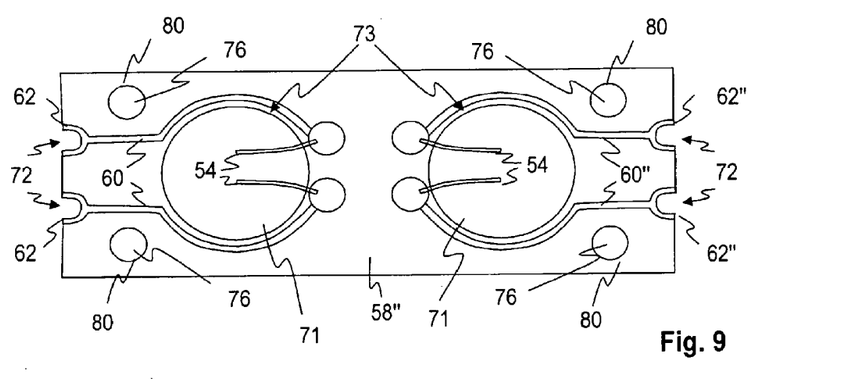

A third embodiment example in FIGS. 8 and 9 differs from the first embodiment example substantially in that the ultrasonic transducer module now possesses, instead of only one ultrasonic transducer 52, two ultrasonic transducers which, in this embodiment example, are like configured and held in like alignment. Because they are like configured, the same reference signs are employed for them and their parts as in the first embodiment example, and the remarks on the ultrasonic transducer of the first embodiment example also apply accordingly here.

The mounting module 50" possesses, as in the first embodiment example, a transducer holder 56" and a circuit board 58". The transducer holder as well as the circuit board 58' are configured mirror-symmetrically with regard to the plane indicated by arrows in FIG. 8 and extending orthogonally to the drawing plane.

The transducer holder 56" has two receiving means 67 for the ultrasonic transducers 52, which are designed as in the first embodiment example. The fastening of the ultrasonic transducers 52 in the receiving means 67 is effected as in the first embodiment example, so that the same reference signs are employed in FIGS. 8 and 9 for identical components as in the first embodiment example and the remarks thereon apply accordingly.

The receiving means 67 in the transducer holder 56" are so configured that the ultrasonic transducers 52 are aligned parallel. Hence, their transmission and reception characteristics 79, which are indicated only very schematically in FIG. 8, are also aligned parallel to each other, so that an ultrasonic sensor with two tracks can be constructed. The characteristics are respectively rotationally symmetric around an axis parallel to the primary transmission or reception direction, so that the axes and thus the primary transmission or reception directions are parallel.

The transducer holder 56" furthermore differs from the transducer holder 56 by positioning elements 76, by means of which and of complementary positioning elements in the connection support 44" the mounting module 50" is positionable on the connection support. Serving as positioning elements 76 here are pins, and as complementary positioning elements 78 in the connection support 44' corresponding holes. The complementary positioning elements 78 are indicated in FIG. 8 by continuous lines.

The circuit board 58" further differs from the circuit board 58 by through holes 80 which are so arranged that upon the connection of the circuit board 58" to the transducer holder 56" its positioning elements reach through the through holes. The diameters of the holes 78 and of the through holes 80 are dimensioned relative to the diameter of the pins 76 such that a certain force closure is also achieved besides a form closure, so that a bonding is optional. These positioning elements thus serve not only for positioning, but can also absorb forces occurring parallel to the connection support, so that the soldered connections are relieved.

The mounting module 50" is hence configured for holding both ultrasonic transducers and has in particular conducting paths 60" which are electrically connected to the connecting strands 54 of the second ultrasonic transducer and have second contact areas which are so configured that the ultrasonic transducer module is placeable for mounting onto the surface of the connection support 44" on which surface there are located second complementary contact areas 66" for the second contact areas 62", and the further contact areas 62" and the complementary further contact areas 66" are solderable to each other. The same applies to the contact areas 62 and the complementary contact areas 66.

The manufacture of the ultrasonic transducer module is effected analogously to the first embodiment example.

Figure 10:
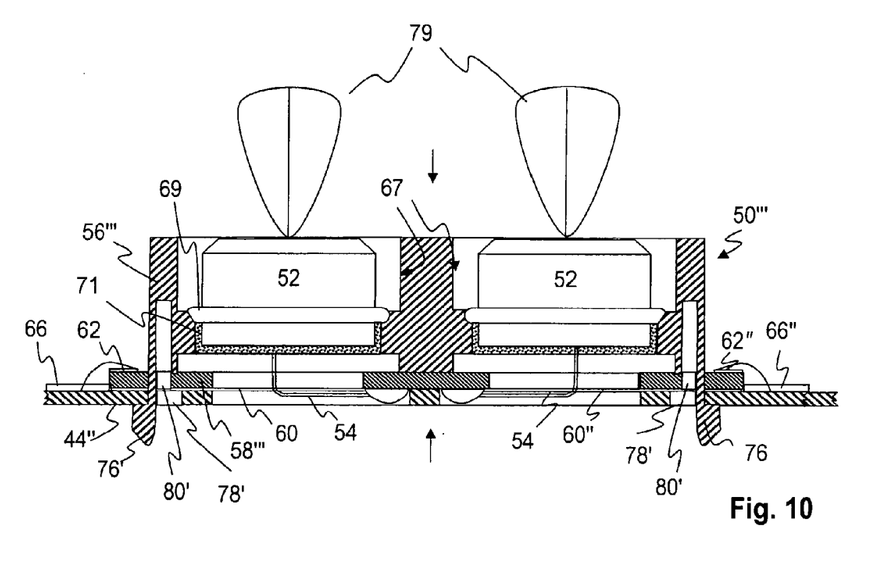

A fourth embodiment example in FIG. 10 differs from the third embodiment example only by the type of the positioning elements and of the complementary positioning elements. The transducer holder 56''' and the circuit board 58''', which are parts of the mounting module 50''', and the ultrasonic transducers 52 are otherwise configured as in the third embodiment example, so that the same reference signs are employed for mutually corresponding components, and the remarks on the components of the third embodiment example also apply here.

The transducer holder 52''' now has, instead of the pins, as positioning elements snapping or locking hooks 76', the connection support as complementary positioning elements 78' accordingly arranged and dimensioned holes. The circuit board 58''' again has through holes 80' which, however, are so dimensioned as to make possible a functioning of the positioning elements, in particular the snapping motion.

The mounting module 50''' can now, after manufacture and checking, be placed onto the connection support 44''', whereby the positioning elements 76' are introduced into the corresponding complementary positioning elements 78' while being deflected and snap back upon reaching of the mounting position. These positioning elements thus serve not only for positioning, but can also absorb forces occurring parallel and orthogonally to the connection support, so that the soldered connections are relieved.

Figure 11:
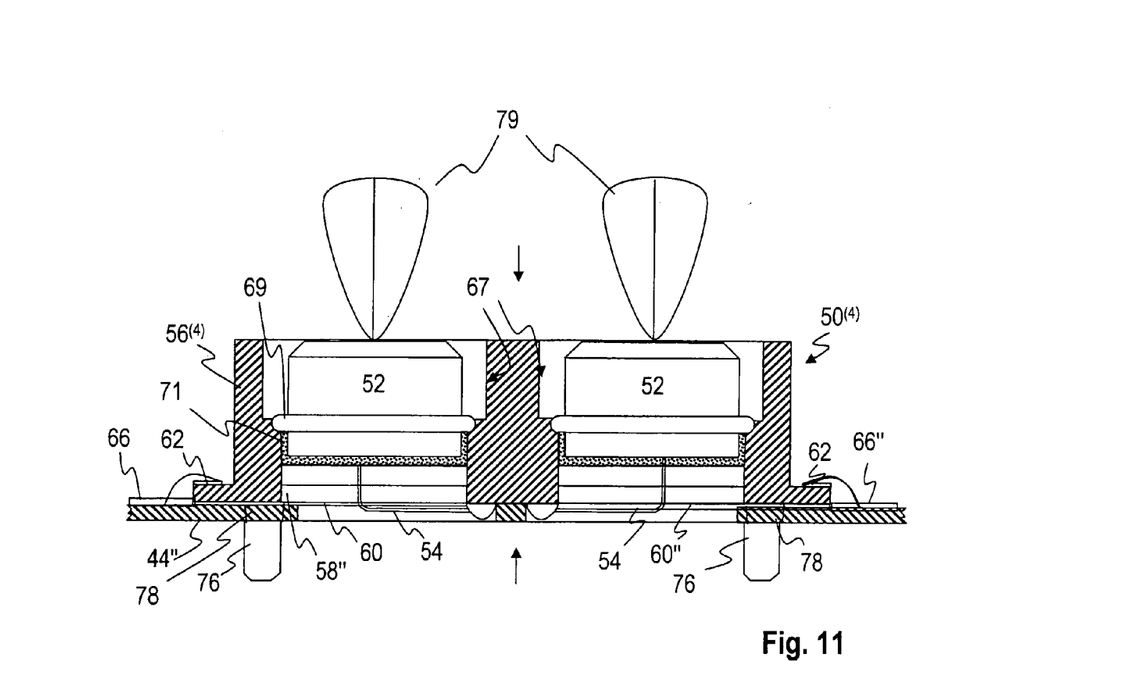
Figure 12:
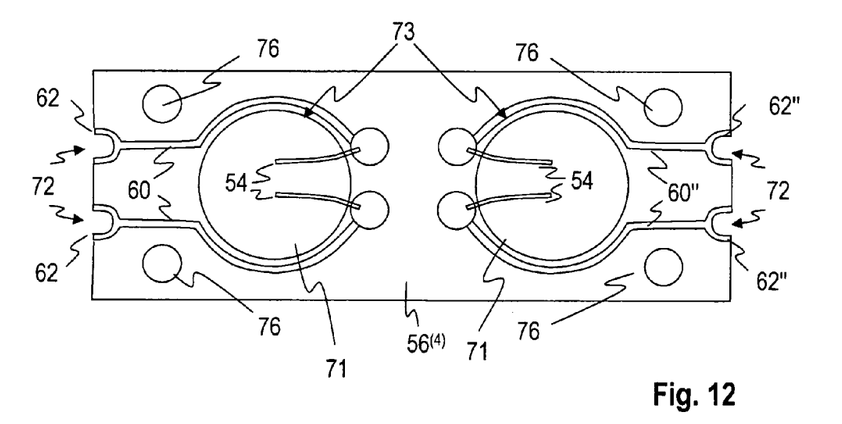

A fifth embodiment example in FIGS. 11 and 12 differs from the third embodiment example in that, instead of the mounting module 50" comprising transducer holder 52" and circuit board 58", the mounting module 50$^{(4)}$ now has a one-pieced holding element 56$^{(4)}$ on whose surface the conducting paths 60$^{(4)}$ extend. Identical reference signs are hence employed for identical or analogous components as in the second embodiment example, and the remarks thereon also apply accordingly here.

The holding element 56$^{(4)}$ is so configured that it replaces transducer holder 52' and circuit board 58'. It has the same form, except for the diameter of the regions corresponding to the through holes 80, as the mounting module formed from the transducer holder 52' and the circuit board 58'.

The holding element 56$^{(4)}$ can preferably be manufactured as an injection molded part. The conducting paths can either be incorporated during injection molding, or be applied to the holding element 56$^{(4)}$ after manufacture thereof, also by other manufacturing methods. This embodiment permits an especially simple manufacture of the ultrasonic transducer module.

In other variants of the last embodiment example, the conducting paths 60 can be realized at least partly by wires and extend within the holder 56$^{(4)}$. They can already be incorporated into the holder during injection molding if the holder is manufactured by injection molding.

The invention claimed is:

1. An ultrasonic transducer module for an ultrasonic sensor for either or both
   detection and examination of value documents, comprising
   at least one piezoelectric ultrasonic transducer having electrical connecting strands, and
   a mounting module arranged to hold the at least one piezoelectric ultrasonic transducer for mounting on a connection support,
   wherein the mounting module includes conducting paths which are electrically connected to the connecting strands of the at least one piezoelectric ultrasonic transducer and which have conducting path contact areas that extend at least partially to a top surface of the mounting module wherein the ultrasonic transducer module is placeable for mounting with its underside onto a surface of the connection support on which surface there are located support contact areas complementary to said conducting path contact areas, and wherein the support contact areas and the conducting path contact areas are solderable to each other.

2. The ultrasonic transducer module according to claim 1, comprising in
   addition to the at least one ultrasonic transducer, a further piezoelectric ultrasonic transducer having electrical connecting strands, and
   wherein the mounting module is configured to hold the ultrasonic transducers and has mounting module conducting paths which are electrically connected to the connecting strands of the further ultrasonic transducer and have further mounting module conductive path contact areas which are so configured that the ultrasonic transducer module is placeable for mounting onto a surface of the connection support on which surface there are located further connection support complementary contact areas for the further mounting module conductive path contact areas, and
   wherein the contact areas are solderable to each other.

3. The ultrasonic transducer module according to claim 2, wherein the ultrasonic transducers respectively have a transmission or reception characteristic for ultrasound, and the transmission and reception characteristics of the ultrasonic transducers are aligned parallel to each other.

4. The ultrasonic transducer module according to claim 1, wherein the mounting module has a transducer holder in which the ultrasonic transducer is held or the ultrasonic transducers are held, and a circuit board connected to the transducer holder and having the conducting paths.

5. The ultrasonic transducer module according to claim 4, wherein the circuit board has at least one through bore through which the connecting strands of the ultrasonic transducer are guided, or has through bores through which the connecting strands of the ultrasonic transducers are guided.

6. The ultrasonic transducer module according to claim 1, wherein the mounting module has a one-pieced holding element, either or both in and on the surface of which, the conducting paths extend.

7. The ultrasonic transducer module according to claim 1, wherein the mounting module has at least one positioning element by means of which, and with a complementary positioning element provided on or in the connection support, the mounting module is positionable on the connection support.

8. The ultrasonic transducer module according to claim 7, wherein the mounting module has a snapping or locking element, or wherein the positioning element is configured as a snapping or locking element, by means of which the mounting module is fastenable on the connection support.

9. The ultrasonic transducer module according to claim 1, wherein the ultrasonic transducer or transducers are held so as to be decoupled from the transducer holder at least partly for vibrating.

10. An ultrasonic sensor for either or both detection and examination of value documents, comprising the ultrasonic transducer module recited in claim 1 and a sensor connection support with sensor support contact areas complementary to the contact areas of the ultrasonic transducer module, wherein the contact areas of the ultrasonic transducer module and the complementary sensor support contact areas of the connection support are soldered to each other.

11. A method for manufacturing an ultrasonic sensor for either or both detection and examination of value documents comprising the steps:
   making the ultrasonic transducer module according to claim 1,
   checking the contact between the connecting strands of the transducer and the contact areas of the mounting module, and
   placing the ultrasonic transducer and mounting module onto the connection support with support contact areas complementary to the contact areas of the ultrasonic transducer module, and
   soldering together the transducer module contact areas and the complementary support contact areas.

* * * * *